(12) United States Patent
Fabo et al.

(10) Patent No.: US 8,497,407 B2
(45) Date of Patent: Jul. 30, 2013

(54) SEALING FILM DRESSING

(75) Inventors: Tomas Fabo, Mölnlycke (SE); Bengt Söderström, Mölndal (SE); Anna Svensby, Göteborg (SE)

(73) Assignee: Molnlycke Health Care AB, Gothenburg (SE)

( * ) Notice: Subject to any disclaimer, the term of this patent is extended or adjusted under 35 U.S.C. 154(b) by 22 days.

(21) Appl. No.: 11/794,988

(22) PCT Filed: Jan. 9, 2006

(86) PCT No.: PCT/SE2006/000025
§ 371 (c)(1),
(2), (4) Date: Oct. 24, 2007

(87) PCT Pub. No.: WO2006/075950
PCT Pub. Date: Jul. 20, 2006

(65) Prior Publication Data
US 2008/0114278 A1    May 15, 2008

(30) Foreign Application Priority Data
Jan. 11, 2005 (SE) ........................ 0500061

(51) Int. Cl.
*A61F 13/00* (2006.01)
(52) U.S. Cl.
USPC .................. 602/48; 602/52; 602/57

(58) Field of Classification Search
USPC .............. 602/48, 41–42, 52, 54–58; 604/313, 604/307, 319; 128/849, 850, 851, 852, 853, 128/854, 855, 856, 857, 858, 859, 860, 861, 128/862, 888; 424/443, 445–449
See application file for complete search history.

(56) References Cited

U.S. PATENT DOCUMENTS

| | | | |
|---|---|---|---|
| 3,367,332 A | 2/1968 | Dibelius et al. | |
| 3,645,835 A | 2/1972 | Hodgson | |
| 3,874,387 A | 4/1975 | Barbieri | |
| 4,308,313 A * | 12/1981 | Groff | ............................ 442/117 |
| 4,310,509 A | 1/1982 | Berglund et al. | |
| 4,372,303 A | 2/1983 | Grossmann et al. | |
| 4,382,441 A | 5/1983 | Svedman | |
| 4,485,809 A | 12/1984 | Dellas | |

(Continued)

FOREIGN PATENT DOCUMENTS

| CA | 1222671 A1 | 6/1987 |
|---|---|---|
| EP | 0051935 B1 | 5/1982 |

(Continued)

OTHER PUBLICATIONS

Australian Office Action dated Jul. 29, 2010 in corresponding 2006205242.

(Continued)

*Primary Examiner* — Patricia Bianco
*Assistant Examiner* — Ophelia A Hawthorne
(74) *Attorney, Agent, or Firm* — Ballard Spahr LLP (57) ABSTRACT

The present invention relates to a film dressing comprising a thin plastic film (2) coated with an adhesive (3). In accordance with the invention, the adhesive (3) has a softness of 10-22 mm, and the adhesive coating has a weight per unit area of 50 g/m² or more.

17 Claims, 9 Drawing Sheets

U.S. PATENT DOCUMENTS

| | | | |
|---|---|---|---|
| 4,595,001 A | 6/1986 | Potter et al. | |
| 4,600,001 A | 7/1986 | Gilman | |
| 4,621,029 A * | 11/1986 | Kawaguchi | 428/447 |
| 4,753,232 A * | 6/1988 | Ward | 602/52 |
| 4,969,880 A | 11/1990 | Zamierowski | |
| 5,052,381 A | 10/1991 | Gilbert et al. | |
| 5,088,483 A | 2/1992 | Heinecke | |
| 5,153,040 A * | 10/1992 | Faasse, Jr. | 428/41.5 |
| 5,160,315 A | 11/1992 | Heinecke et al. | |
| 5,514,435 A * | 5/1996 | Suzuki et al. | 428/41.5 |
| 5,531,855 A | 7/1996 | Heinecke et al. | |
| 5,540,922 A * | 7/1996 | Fabo | 424/402 |
| 5,549,584 A | 8/1996 | Gross | |
| 5,635,201 A | 6/1997 | Fabo | |
| 5,738,642 A | 4/1998 | Heinecke et al. | |
| 5,755,681 A * | 5/1998 | Plews | 602/58 |
| 5,827,246 A | 10/1998 | Bowen | |
| 5,891,076 A * | 4/1999 | Fabo | 602/52 |
| 5,994,613 A | 11/1999 | Cummings et al. | |
| 6,117,111 A * | 9/2000 | Fleischmann | 604/180 |
| 6,124,520 A | 9/2000 | Roberts | |
| 6,124,521 A | 9/2000 | Roberts | |
| 6,169,224 B1 | 1/2001 | Heinecke et al. | |
| 6,207,875 B1 | 3/2001 | Lindqvist et al. | |
| 6,387,082 B1 | 5/2002 | Freeman | |
| 6,458,109 B1 | 10/2002 | Henley et al. | |
| 6,479,724 B1 * | 11/2002 | Areskoug et al. | 602/41 |
| 6,607,995 B1 * | 8/2003 | Takeuchi et al. | 442/216 |
| 6,620,132 B1 | 9/2003 | Skow | |
| 6,685,682 B1 | 2/2004 | Heinecke et al. | |
| 6,706,940 B2 | 3/2004 | Worthley | |
| 6,755,807 B2 | 6/2004 | Risk, Jr. et al. | |
| 6,797,855 B2 | 9/2004 | Worthley | |
| 6,841,715 B2 | 1/2005 | Roberts | |
| 6,866,949 B2 * | 3/2005 | Ota et al. | 428/702 |
| 6,960,181 B2 | 11/2005 | Stevens | |
| 6,998,511 B2 | 2/2006 | Worthley | |
| 7,004,915 B2 | 2/2006 | Boynton et al. | |
| 7,049,479 B2 | 5/2006 | Cleary et al. | |
| 7,094,944 B2 | 8/2006 | Faasse, Jr. | |
| 7,108,683 B2 | 9/2006 | Zamierowski | |
| 7,161,056 B2 | 1/2007 | Gudnason et al. | |
| 7,300,424 B1 | 11/2007 | Mulford | |
| 7,381,859 B2 | 6/2008 | Hunt et al. | |
| 7,532,953 B2 | 5/2009 | Vogel | |
| 7,645,269 B2 | 1/2010 | Zamierowski | |
| 7,645,916 B2 | 1/2010 | Rasor | |
| 7,651,484 B2 | 1/2010 | Heaton et al. | |
| 7,670,323 B2 | 3/2010 | Hunt et al. | |
| 7,722,582 B2 | 5/2010 | Lina et al. | |
| 7,759,538 B2 | 7/2010 | Fleischmann | |
| 7,815,616 B2 | 10/2010 | Boehringer et al. | |
| 7,846,141 B2 | 12/2010 | Weston | |
| 2003/0124343 A1 | 7/2003 | Murakami et al. | |
| 2004/0102744 A1 * | 5/2004 | Fattman | 604/344 |
| 2004/0126413 A1 | 7/2004 | Sigurjonsson et al. | |
| 2004/0220505 A1 | 11/2004 | Worthley | |
| 2005/0205099 A1 * | 9/2005 | Gellerstedt et al. | 128/849 |
| 2005/0283105 A1 | 12/2005 | Heaton et al. | |
| 2006/0228318 A1 | 10/2006 | Fabo | |
| 2006/0282034 A1 | 12/2006 | Faasse | |
| 2007/0032762 A1 | 2/2007 | Vogel | |

FOREIGN PATENT DOCUMENTS

| | | |
|---|---|---|
| EP | 0144891 B1 | 6/1985 |
| EP | 0300620 A1 | 1/1989 |
| EP | 0308122 B1 | 3/1989 |
| EP | 0507459 B1 | 10/1992 |
| EP | 0690706 A1 | 1/1996 |
| EP | 0 399 520 B1 | 11/1996 |
| EP | 1 424 088 A1 | 6/2004 |
| GB | 1280631 A | 7/1972 |
| GB | 2 192 142 B | 11/1990 |
| SE | 440314 B | 7/1985 |
| SE | 526906 C2 | 11/2005 |
| WO | WO-80/01139 A1 | 6/1980 |
| WO | 9319710 A1 | 10/1993 |
| WO | 9609076 A1 | 3/1996 |
| WO | WO-99/61077 A1 | 12/1999 |
| WO | WO-99/61078 A1 | 12/1999 |
| WO | WO-00/76440 A1 | 12/2000 |
| WO | WO-02/028447 B1 | 9/2002 |
| WO | WO-03/079919 A1 | 10/2003 |
| WO | WO-2004/018020 A1 | 3/2004 |
| WO | WO-03/079920 A8 | 5/2004 |
| WO | WO-2004/047695 A1 | 6/2004 |
| WO | WO-2004/108175 A1 | 12/2004 |
| WO | WO-2005/007020 A2 | 1/2005 |
| WO | WO-2005/009371 A2 | 2/2005 |
| WO | WO-2006/046060 A2 | 5/2006 |
| WO | WO-2006/048240 A1 | 5/2006 |
| WO | WO-2006/075950 A1 | 7/2006 |

OTHER PUBLICATIONS

International Search Report with Written Opinion issued on Apr. 27, 2006 for Intl. App. No. PCT/SE2006/000025, filed on Jan. 9, 2006 (Inventor—T. Fabo et al.; Applicant—Mölnlycke Health Care AB; pp. 1-7).

International Preliminary Report on Patentability issued on Jul. 17, 2007 for Intl. App. No. PCT/SE2006/000025, filed on Jan. 9, 2006 (Inventor—T. Fabo et al.; Applicant—Mölnlycke Health Care AB; pp. 1-5).

International Search Report with Written Opinion issued on Oct. 15, 2007 for Intl. App. No. PCT/SE2007/050484, filed on Jul. 2, 2007 (Inventor—A. Svensby et al.; Applicant—Mölnlycke Health Care AB; pp. 1-7).

International Preliminary Report on Patentability issued on Jan. 13, 2009 for Intl. App. No. PCT/SE2007/050484, filed on Jul. 2, 2007 (Inventor—A. Svensby et al.; Applicant—Mölnlycke Health Care AB; pp. 1-7).

Response to Non-Final Office Action filed on Feb. 29, 2012 for U.S. Appl. No. 12/305,590, filed Feb. 20, 2009; Inventor—A. Svensby et al.; pp. 1-19).

Non-Final Office Action issued on Sep. 30, 2011 for U.S. Appl. No. 12/305,590, filed Feb. 20, 2009; Inventor—A. Svensby et al.; pp. 1-22).

Preliminary Amendment filed on Dec. 18, 2008 for U.S. Appl. No. 12/305,590, filed Feb. 20, 2009; Inventor—A. Svensby et al.; pp. 1-12).

Webpage, "Internet google book search re: hollister medical adhesive dressings", retreived from http://www.r.google.com/search?q=hollister+medicain+silicone+adhesive&btnG=Searc . . . on Jun. 18, 2012, pp. 1-2.

Webpage, "Polydimethylsiloxane", retrieved from http://en.wikipedia.org/wiki/Polydimethylsiloxane on Jun. 6, 2012, pp. 1-5.

Cinar et al., "Blood Viscoscity and Blood Pressure: Role of Temperature and Hyperglycemia," *American Journal of Hypertension*, 2001; 12:433-438.

American Society for Testing and Materials, "ASTM 666-94: Standard Specification for Austenitic Stainless Steel Sheet, Strip, Plate, and Flat Bar", Oct. 1994, pp. 1-6.

"Hollister Product Parade", advertisement in *Journal Drug Intelligence & Clinical Pharmacy*, 1973, pp. 247.

Satas, D. eds., "Silicone Pressure Sensitive Adhesives", Handbook of Pressure Sensitive Adhesive Technology, 2nd Edition 1989, pp. 515-517.

Handbook of Chemistry and Physics, 76th Edition, 1995, pp. 6-10; 6-155-6-158.

Webpage, "Amazon.com: Remington: The Science and Practice of Pharmacy (9780781746731): . . . ", retrieved from http://www.amazon.com/Remington-The-Science-Practice-Pharmacy/dp/0781746736 on Jun. 18, 2012, pp. 1.

Tipler, P., "Solids and Fluids", *Physics*, Worth Publishers, New York, 1982, pp. 382-384, 390-391.

Webpage, "Plastic Material Data Sheet (Knovel) about Dow Coming 7355 silicone adhesive", undated reference, pp. 1.

Webpage, "Safetac technology", printout of Patentee's webpage "Tendra Startpage>Products>Safetac Technology" from Apr. 29, 2003 as captured from WayBackMachine, retrieved from http://web.

archive.org/web/20030429170256fw_/http://tendra.com/item. asp?id=1015&lang=2 on Jun. 18, 2012, pp. 1-7.

Webpage, "Dressings", printout of Patentee's webpage "Tendra Startpage>Products>Safetac Technology>Dressings" from May 5, 2003 as captured from WayBackMachine, retrieved from http://web.archive.org/web/20030505042240/http://www.tendra.com/item. asp?id=1021&lang=2 on Jun. 18, 2012, pp. 1-9.

Webpage, screenshots of Patentee's webpage "Tendra Startpage>Products>Safetac Technology>Silicone" from May 5, 2003 as captured by the WayBackMachine, undated reference, pp. 1-2.

Glatfelter, "Paper: Moisture and Relative Humidity", Glatfelter Technical Bulletin, Issue Feb. 2005, Rev. 05/05, pp. 1-12.

3M, "TEGADERM™ and TEGADERM™ HP Transparent Dressings", Product Brochure, 2004, pp. 1-2.

Harkins, H. et al., "The Surface Tension of Blood Serum, and the Determination of the Surface Tension of Biological Fluids", *The Journal of Clinical Investigation*, 1929, vol. VII, No. 2, pp. 263-281.

"Part 5: Pharmaceutical Manufacturing", *Remington: The Science and Practice of Pharmacy*, 21st Edition, Lippincott Williams & Wilkins Publishers, 2005, pp. 948.

Pocius, A.V., "The Chemistry and Physical Properties of Elastomer-Based Adhesives", *Adhesion and Adhesives Technology*, 2nd Edition, Hanser Publishers, Cincinnati, 2002, pp. 238-242.

Wacker Silicones, "WACKER SilGel™ 612", product datasheet, Sep. 2, 2004, pp. 1-3.

Notice of Opposition filed by Third Party on Jun. 28, 2012 for EP Pat. No. 1845912, national phase of Intl. App. No. PCT/SE2006/000025, filed on Jan. 9, 2006 (T. Fabo et al.; Molnlycke Health Care AB; pp. 1-12)

Notice of Opposition filed by Third Party on Jun. 21, 2012 for EP Pat. No. 1845912, national phase of Intl. App. No. PCT/SE2006/000025, filed on Jan. 9, 2006 (T. Fabo et al.; Molnlycke Health Care AB; pp. 1-27).

Decision to grant European patent issued on Sep. 1, 2011 for EP Pat. App. No. 06700864.9, national phase of Intl. App. No. PCT/SE2006/000025, filed on Jan. 9, 2006 (T. Fabo et al.; Molnlycke Health Care AB; pp. 1-2).

Intention to grant European patent issued on Apr. 14, 2011 for EP Pat. App. No. 06700864.9, national phase of Intl. App. No. PCT/SE2006/000025, filed on Jan. 9, 2006 (T. Fabo et al.; Molnlycke Health Care AB; pp. 1-39).

Preliminary Amendment and Response filed on Nov. 25, 2010 for EP Pat. App. No. 06700864.9, national phase of Intl. App. No. PCT/SE2006/000025, filed on Jan. 9, 2006 (T. Fabo et al.; Molnlycke Health Care AB; pp. 1-8).

Extended European Search Report and Search Opinion issued on May 6, 2010 for EP Pat. App. No. 06700864.9, national phase of Intl. App. No. PCT/SE2006/000025, filed on Sep. 9, 2006 (T. Fabo et al.; Molnlycke Health Care AB; pp. 1-8).

Final Office Action issued on Jul. 23, 2012 for U.S. Pat. App. No. 12/305,590, filed on Feb. 20, 2009 (A. Svensby; pp. 1-36).

Extended European Search Report with Written Opinion issued Jun. 21, 2012 for EP Pat. App. No. 07769030.3, national phase of Intl. App. No. PCT/SE2007/050484, filed on Jul. 2, 2007 (A. Svensby et al.; Molnlycke Health Care AB; pp. 1-4).

Response to Notices of Opposition filed by Applicant on Nov. 30, 2012 for EP Pat. No. 1845912 (EP App. No. 06700864.9), national phase of Intl. App. No. PCT/SE2006/000025, filed on Jan. 9, 2006 (T. Fabo et al.; Molnlycke Health Care Ab; pp. 1-39).

* cited by examiner

SEALING FILM DRESSING

TECHNICAL FIELD

The present invention relates to a film dressing comprising a thin plastic film coated with an adhesive.

BACKGROUND ART

At the start of the 1980s, a new type of wound dressing was launched by Smith&Nephew, a company which manufactures wound dressing products. The product, which is still on the market and is sold under the name OpSite™, is based on an invention that is described in British patent GB1280631. The dressing consists of a very thin polyurethane film, ca 25 micrometres, that is coated with a thin, self-adhesive layer of adhesive, also ca 25 micrometres. Due to its thinness, the film is very flexible and pliant. It can be attached securely and can seal relatively tightly around wounds on non-smooth skin surfaces, both convex and concave. Any wrinkles that are formed, however, sometimes produce thin channels, through which fluid is able to leak. This dressing, which was totally unlike all previous dressing products, formed an entirely new category known as self-adhesive film dressings. More companies followed with similar products, and today large numbers of film products with a similar function and characteristics are available on the market. These film dressings soon found an important application for the securing and protection of intravenous cannulas (for example of the Venflon cannula type). They are also used to cover different types of wound, for example sites from which skin is removed in conjunction with skin transplantation.

A significant factor for the major sales success of the film products was, apart from the above-mentioned characteristics, the successful development of effective application systems. The thin dressings are extremely difficult to handle without specially designed application systems. For this purpose, therefore, a more rigid carrier material is normally attached in a removable fashion to the non adhesive-coated side of the film in order to impart rigidity to the product, which would otherwise easily become tangled up in conjunction with its application to the skin. The carrier material, which imparts rigidity to the thin film, is not removed from the product until the self-adhesive film has been applied in the intended place.

The film dressings have been improved in a variety of ways in more recent times. Specially designed intravenous securing films have been developed with a perforated narrow slot to leave space for the tube connection of the intravenous cannula and, in so doing, to improve its function. A number of film dressings have been provided with a wound pad which covers the central part of the adhesive-coated side (a so-called island dressing), so that a certain degree of absorption of fluid from the wound is achieved when the film dressing is applied over a wound.

The above-mentioned category of dressing, self-adhesive film dressings, has nevertheless shown itself to have a number of weaknesses:

1. Relatively aggressive adhesives have been used in order to achieve a secure fixing without the risk of the film dressings becoming loose. The manufacturers selected aggressive types of adhesive in order to satisfy themselves that the dressings are already attached to the skin sufficiently securely immediately after application. The reason for this is to avoid the intravenous cannula becoming loose inadvertently, which would constitute a risk to the safety of the patient. It is also wished to avoid wound fluid from weeping wounds penetrating the adhesive joint between the film and the skin and leaking out onto the healthy skin outside the dressing. The types of adhesive used today possess the characteristic that the adhesion to the skin increases substantially with time. The adhesive strength of many film dressings is multiplied several times over after a few hours or days, compared with the adhesion immediately after application. When film dressings are attached too strongly, they often cause reddening and pain when they are removed from the skin. They also damage the barrier function of the skin because they take with them epithelial cells from the skin. In spite of this, a manufacturer may select these types of adhesive because the most important consideration is for the adhesion to be sufficiently good directly after application.

2. In the course of examining the protection against leakage from film dressings, the applicants identified an unexpected weakness in the ordinary film dressings. Studies under the microscope revealed that fluids are capable of spreading easily under the film dressings, in spite of the fact that they are apparently securely attached to the skin with an entirely tight seal. It was found that fluid was capable of spreading for a number of centimetres under the dressings via the naturally occurring microscopic folds in normal skin. Because the leakage consists of very small quantities and is not visible if the inward leakage of colourless fluids is examined, this has been disregarded previously. The phenomenon, known as micro-leakage, was first observed when the fluid was dyed with a strongly coloured pigment. The transport of fluids beneath the film dressings can constitute a major risk to patients because micro-organisms could be transported from outside or from the skin under the dressing and into the wound. An infection from a central venous catheter (CVC), which will often have been covered with a film dressing, can constitute a risk to the patient's life. Manufacturers of film dressings often market these as "shower proof". When taking a shower, the risk of the aforementioned type of micro-leakage naturally increases considerably.

3. The adhesive on the film dressings that are sold today exhibits high adhesion to hairs. Because these dressings are often applied to hairy skin surfaces, pain and pulling out of hairs often occurs when the dressings are removed.

The object of the present invention is to solve the aforementioned problems while retaining all the advantages offered by the thin elastic carrier material, such as their softness and pliability, which is the unique strong feature of the film dressing product type.

DISCLOSURE OF INVENTION

This object is achieved by means of a film dressing comprising a thin plastic film coated with an adhesive, characterized in that the adhesive has a softness of 10-22 mm, and in that the adhesive coating has a weight per unit area of 50 g/m$^2$ or more. Micro leakage is prevented by the fact that the adhesive coating has a high weight per unit area and the adhesive has high softness. Soft adhesives also exhibit the right level of adhesion directly after application, and the adhesion increases either not at all or only slightly with time. Adhesion to hairs is also so low that the hairs remain in place almost without exception.

In a preferred illustrative embodiment, the adhesive consists of a silicone elastomer or, alternatively, a hot-melt adhesive.

The film dressing is also leakproof in accordance with the MHC Leakage Test with a groove depth of 75 micrometres.

The thickness of the plastic film is less than 50 micrometres. The plastic film preferably has a thickness of 12-25 micrometres and a bending rigidity of less than 3 mm, and preferably less than 1.8 mm.

The strength of adhesion to steel of an applied dressing preferably does not vary by more than 5% during the period from 1 minute to 48 hours.

BRIEF DESCRIPTION OF DRAWINGS

The invention is described below with reference to the accompanying Figures, in which.

MODE(S) FOR CARRYING OUT THE INVENTION

Figure 1:
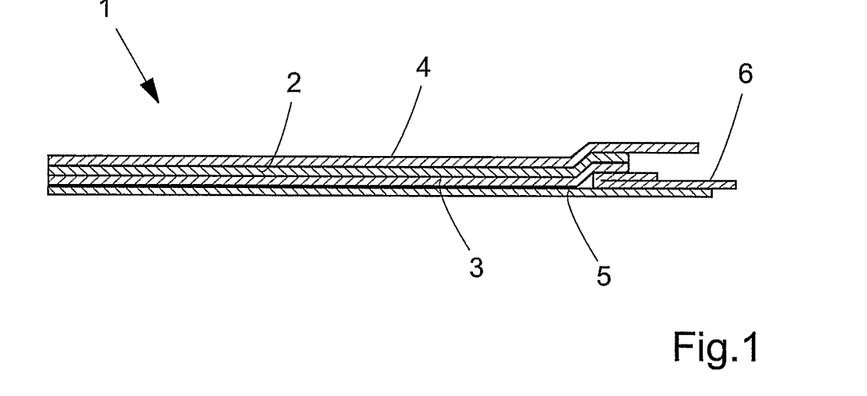
FIG. 1 illustrates schematically a cross-sectional view through a film dressing in accordance with a preferred embodiment of the invention.

Illustrated in FIG. 1 is a cross-sectional view of a film dressing 1 in accordance with a preferred embodiment of the invention. The dressing consists of a thin plastic film layer 2 preferably made of polyurethane plastic, which is coated with a layer 3 of a soft, skin friendly adhesive. The thickness of the plastic film preferably lies between 12 and 25 micrometres, and is less than 50 micrometres in any case. The weight per unit area of the adhesive layer is equal to or greater than 50 g/m².

The plastic film also has a bending rigidity of less than 3 mm, and preferably less than 1.8 mm, measured using a method as described below.

A carrier layer 4 is also applied above the film layer 2, that is to say on the side facing away from the adhesive layer 3, in order to facilitate application of the film dressing. The function of the carrier layer is to stiffen up the film dressing comprising an adhesive-coated thin plastic film, and the carrier layer can consist of, for example, a polyethylene film or a polyethylene-coated paper with the polyethylene layer facing towards the film, and with a thickness of 50-300 micrometres. The adhesive layer 3 is protected in a customary fashion by a protective layer 5,6 of a material with low adhesion to the adhesive, for example a polyethylene-coated paper or a polyethylene film.

The carrier layer 4 is preferably co-extruded together with the film, or the film may be formed on the carrier layer.

In conjunction with the application of the film dressing 2,3, the protective layer 5 is first removed, after which the dressing is positioned on the user's skin. The protective layer 6 is then removed, and that part of the dressing that was attached to the layer 6 is pressed securely onto the skin. Finally, the carrier layer 4 is removed.

Figures 12, 13:
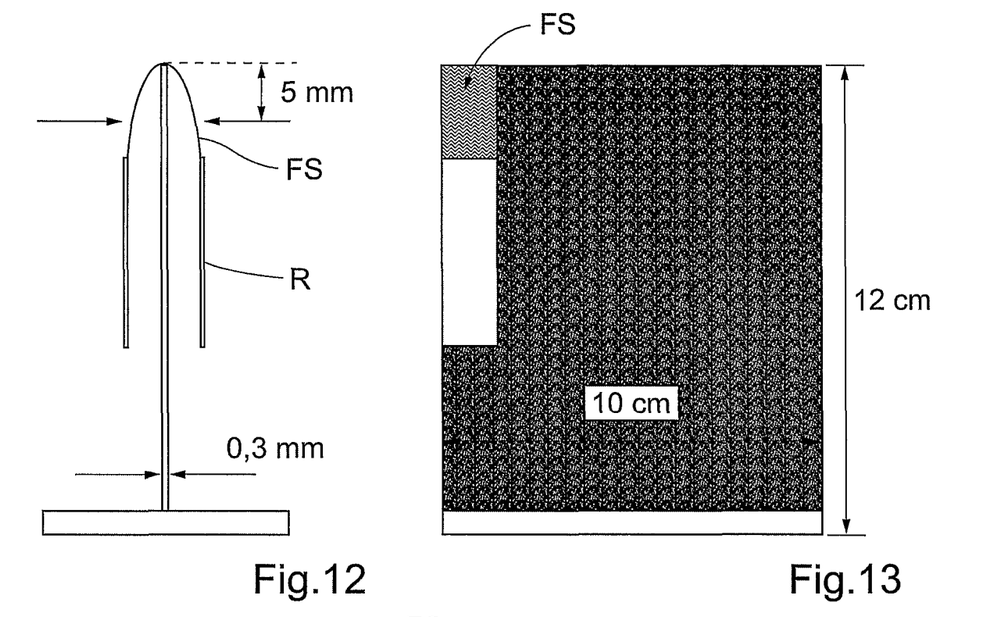
FIGS. 12-14 illustrate a method of measuring the bending rigidity of a plastic film.
Figure 14:
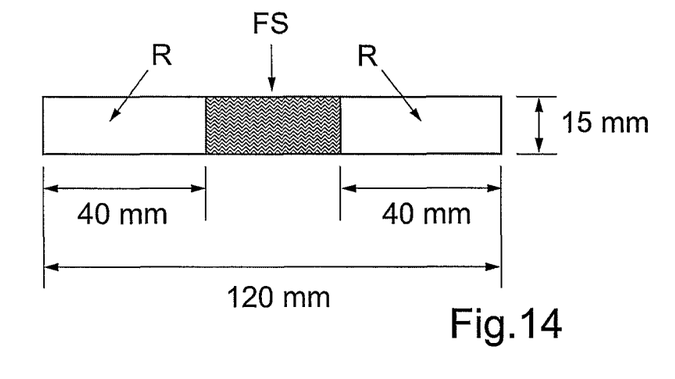

The bending rigidity of the plastic film is determined by the method described below. As shown in FIGS. 12 and 13, in a view respectively from the front and from the side, a test test piece FS, having dimensions of 15×120 mm, is hung over the edge of a 0.3 mm thick metal sheet. The ends of the test piece FS are reinforced with pieces R of two-sided adhesive tape and copying paper having dimensions of 15×40 mm (weight=0.13 g); see FIG. 14. It is important for the sample to be hung over the metal sheet in such a way that the sample hangs down by the same amount on both sides of the metal sheet. After 30 seconds, a picture of the sample hanging as shown in FIG. 12 is taken with a digital camera. A calibrated ruler is appropriately positioned so that it is included in the photograph. The bending rigidity is then determined from the photograph that has been taken by measuring the distance between the ends of the sample at a point 5 mm below the topmost part of the sample. The greater the distance between the ends of the sample, the higher is the bending rigidity exhibited by the sample FS. In order for the plastic film together with the soft adhesive to be capable of following all unevennesses in the skin, the bending rigidity of the film must be less than 3 mm, and must preferably be less than 1.8 mm.

A principal function of the adhesive coating 3 is to attach the film dressing 1 tightly to the skin of the patient, so that the fluid-borne transport of bacteria between the skin and the adhesive coating is prevented, and to attach the film dressing securely to the skin, so that the product remains in place during all the normal loadings to which film dressings are subjected.

The adhesive in the coating must also be skin friendly and must permit removal of the film dressings without causing damage to the skin. This requirement presents a major problem in the case of those types of pressure-sensitive adhesive that are currently used as adhesive coatings for film dressings. Such adhesives often attach themselves to the skin so strongly that parts of the Stratum Corneum, that is to say the uppermost layer of the skin, become stuck to the adhesive and are pulled away from the skin when the attachment of the film dressing is released. This can lead to irritation of and damage to the skin, especially for patients with a sensitive skin, for example patients aged over 70 years, children aged under 3 years, and patients with certain illnesses, such as eczema, or who are undergoing certain treatments, such as cortisone treatment.

The silicone elastomer is very soft and possesses low surface energy, and it adapts very well to the skin, that is to say it flows out into any unevennesses in the skin and creates a large contact surface between the skin and the silicone elastomer. This large contact surface helps the silicone elastomer to become attached securely to the skin, in spite of the fact that the strength of the adhesive attachment of the silicone elastomer to the skin is not in itself so strong. The adhesive strength constitutes a measure of the energy required in order to separate/pull off the adhesive layer from the skin. A contributory factor to the fact that high energy, and thus a high pulling force, are required in order to remove the silicone elastomer from the skin, in spite of the relatively weak strength of the adhesive attachment, is that a lot of energy is consumed in stretching the soft silicone elastomer before it releases from the skin. The softer and thicker the layer of silicone elastomer, the greater the force/energy required to remove the elastomer from the skin.

The use of a harder adhesive will require a stronger strength of adhesive attachment in order for the pulling force to be as high as for a softer adhesive. A strong adhesive attachment between the skin and the adhesive can easily lead to skin cells being pulled from the skin in conjunction with the removal of the adhesive.

Another disadvantage associated with harder adhesives is that these are capable of flowing outwards eventually and thus increasing the size of the contact surface with the skin, with the result that the pulling force eventually increases, which can lead to such adhesives eventually becoming difficult to remove from the skin. Unlike harder adhesives, softer adhesives such as silicone elastomers achieve their full adhesive strength all at once so that their pulling force remains constant as time passes.

Because the characteristics of the skin vary from person to person, the adhesive capacity of the adhesive coating to the skin naturally also varies for different patients. The adhesive strength is also dependent on the thickness of the soft adhesive and the mechanical characteristics of the barrier layer. The standard methods for the measurement of adhesion that are available today use plates of various kinds, for example made of steel or glass, and they do not produce values that are relevant for the measurement of the adhesion to the skin. The values for the strength of the adhesive attachment of an adhesive to the skin, as indicated below, must be measured by means of a method of the kind illustrated schematically in FIG. 2 and developed by the applicants.

Figure 2:
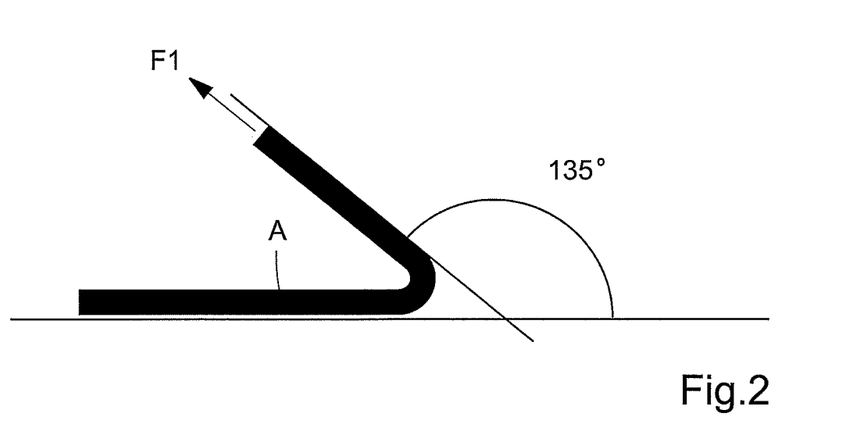
FIG. 2 illustrates schematically the measurement of the strength of adhesion to the skin.

Strips of a self-adhesive film dressing, for which the strength of the adhesive attachment to the skin is to be measured, are punched out with dimensions of 25×125 mm. It should be noted that all the strips are also provided with a carrier layer on the rear side of the film dressing. (The function of this carrier layer is to stiffen up the strips when they are applied to the skin). The strips are then applied to the skin on the back of healthy volunteers. The strips are carefully smoothed into place with a finger, and the carrier layer on the rear side of the strips is then removed. Finally, the strips are pressed securely against the skin for 3 seconds with the help of a sponge made of foam plastic (42×182 mm, thickness=48 mm) glued securely to a steel sheet (50×200 mm, thickness=1 mm). The applied pressure is estimated at 6 kN/m². The strips are left in place on the skin for 2 minutes. The strips are then pulled off at a rate of 25 mm/sec, and the removal force F1 is measured. The angle of removal, that is to say the obtuse angle that is formed between the surface of the skin and the removed part of the strip, must be 135°. The strength of the adhesive attachment of the strip to the skin is constituted by the mean value of the force F1.

Adhesives that are suitable for use in film dressings in accordance with the invention must exhibit a strength of adhesive attachment of at least 0.2-3 N/25 mm in accordance with this method. The strength of adhesive attachment is preferably 1-2.5 N/25 mm.

Figure 3:
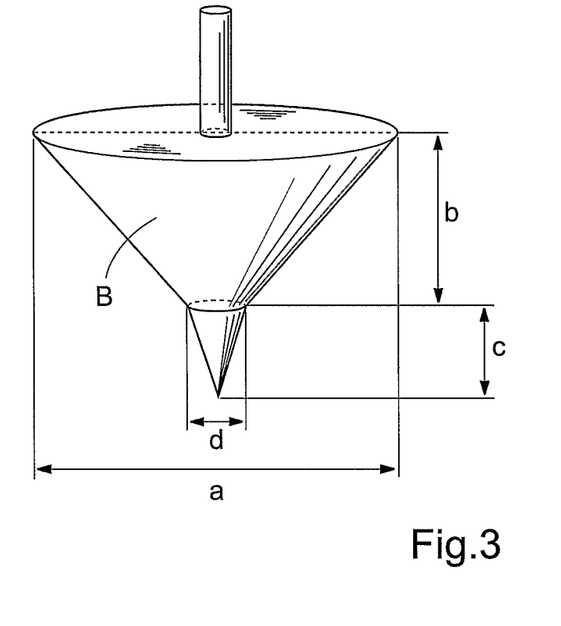
FIG. 3 shows a cone used for softness measurement.
Figure 4:
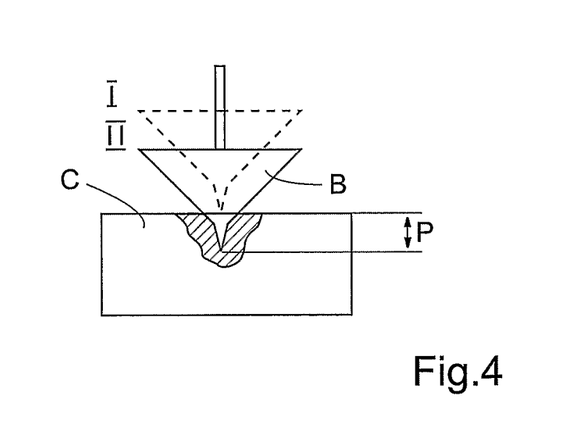
FIG. 4 illustrates a method of measurement for measuring softness.

Adhesives in accordance with the present invention must exhibit a softness that exceeds 10 mm measured by means of a method based on ASTM D 937 and ASTM D 51580. Certain deviations, as can be appreciated below, have been made. FIGS. 3 and 4 illustrate this modified method of measuring the softness of an adhesive by causing a cone B with a weight of 62.5 g to penetrate down by the effect of gravity into a 30 mm thick test piece C of the adhesive for which the softness is to be determined. The test piece is obtained by filling a cylindrical glass container having an internal diameter of 60 mm and an internal height of 35-40 mm, with adhesive to a depth of 30 mm. In the case of a silicone elastomer, it is necessary to fill a non-cured silicone prepolymer into the container, and then to cross-link it to an elastomer in the glass cylinder. The cone used is illustrated in FIG. 3 and has the following dimensions: a=65 mm, b=30 mm, c=15 mm and d=8.5 mm. In the performance of the method for measurement of the softness, the cone B is first lowered down into a position I, as illustrated with broken lines in FIG. 4, and in which the tip of the cone just touches the surface of the test piece C. The cone B is then released, so that it is able to penetrate down into the test piece C by the effect of gravity. The number of millimeters by which the tip B of the cone has penetrated into the test piece C after 5 seconds is measured and constitutes the penetration value P, the value of which is greater in proportion to the softness of the test piece. The penetration value P represents the softness index used in the present invention. A PNR 10 penetrometer supplied by Sommer & Runge KG, Germany is used in the performance of the method.

It has also been found that, in the case of soft, skin friendly adhesives, which form barriers preventing fluid from flowing through them, fluid is capable of leaking through these barriers via cracks in the skin, folds in the skin or other unevennesses in the skin. This leakage can give rise to the propagation of bacteria, which in turn can lead to wound infections.

Surprisingly, it has been found that the above-mentioned risk of leakage can be eliminated, or at least significantly reduced, for a skin friendly adhesive if the adhesive is sufficiently soft and possesses a sufficiently high weight per unit area.

Figure 5:
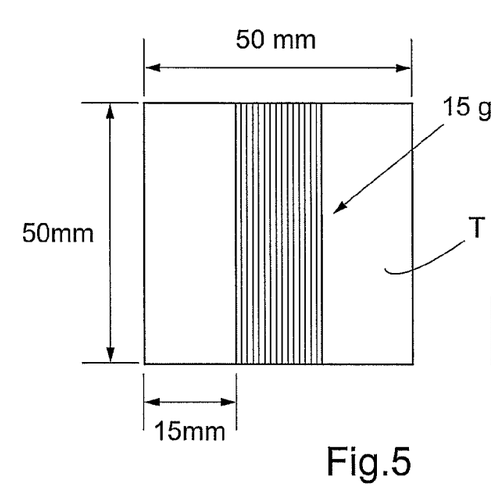
FIGS. 5-11 illustrate the MHC Leakage Test.
Figure 6:
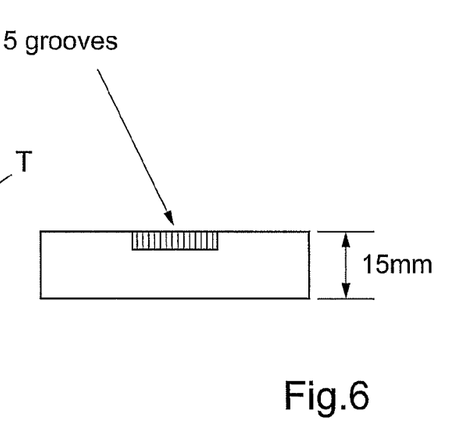

The method described below, known as the MHC Leakage Test, was developed by the applicants for the purpose of determining whether or not a film dressing is leakproof. Specimens S with a size of 30×30 mm and a circular hole (d=12 mm) at the centre of the samples are punched from the dressing to be tested. A coloured test fluid is prepared by mixing 0.2% by weight of Patentblåatt V (from VWR International, Sweden) and 0.1% by weight of Teepol Gold (from Teepol Products, UK) with de-ionized water. An aluminium test plate T having dimensions of 15×50×50 mm and provided with 15 milled grooves is made; see FIG. 5, which shows a plan view of the top side of the plate, and FIG. 6, which shows a view from the side of the plate. For a more detailed description of the form of the grooves, see FIG. 7, which shows a cross-sectional view through a part of the plate.

Figure 7:
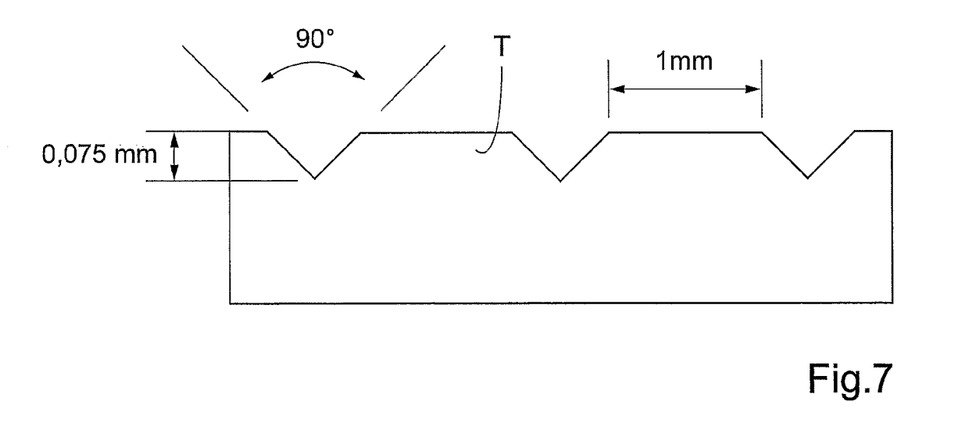

In FIG. 7, the depth of the grooves is 75 micrometres, although other groove depths can be used if it is wished to test the protection against leakage at cracks in the skin or folds in the skin with other depths, for example 50 micrometres or 150 micrometres.

Figure 8:
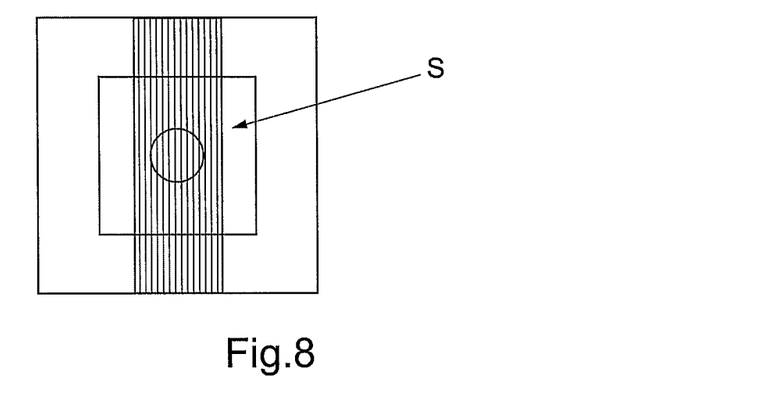

A specimen S is then carefully positioned centrally above the grooves of the test plate T in such a way that no air bubbles occur between the test plate and the specimen; see FIG. 8. No pressure may be exerted on the sample when it is positioned against the plate, so that, in the event that air bubbles occur, these must not be forced away with the help of the fingers, but the sample must be raised and repositioned, or else scrapped.

Figure 9:
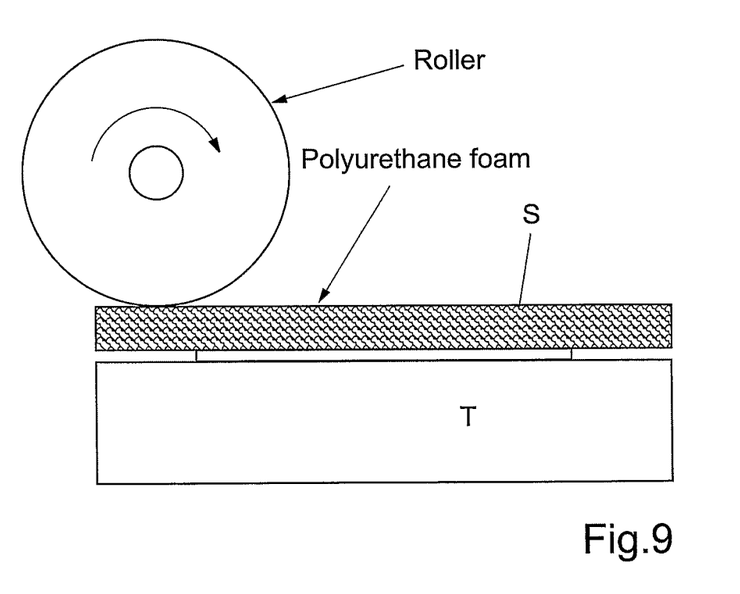

A piece of polyurethane foam (L00562-6, 1.6 mm from Rynel, Inc., Boothbay, Me., USA) having dimensions of 50×50 mm is then placed above the sample S and the test plate T. A mangle made of metal (44 mm wide, r=48 mm, weight=995 g) is then rolled over the foam and the specimen at a speed of 5 mm/second; see FIG. 9. The mangle is rolled back and forth once over the sample.

The piece of foam is removed from the sample S, and 65 μl of the test fluid are placed in the hole on the specimen with the help of a pipette. The test fluid is distributed uniformly in the hole with the help of the tip of the pipette, so that the fluid reaches every point on the edge of the sample. A stop watch is started as soon as all the test fluid is uniformly distributed in the hole. After 30 minutes, a picture is taken with a digital camera of the specimen S and the test fluid T placed on the test plate together with a calibrated ruler.

Figure 10:
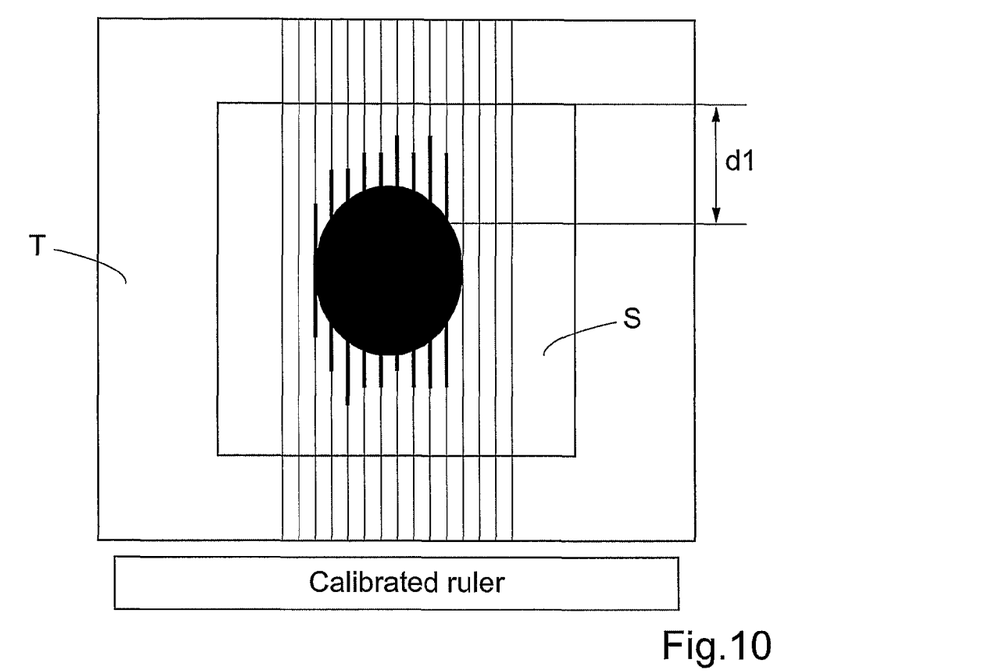
Figure 11:
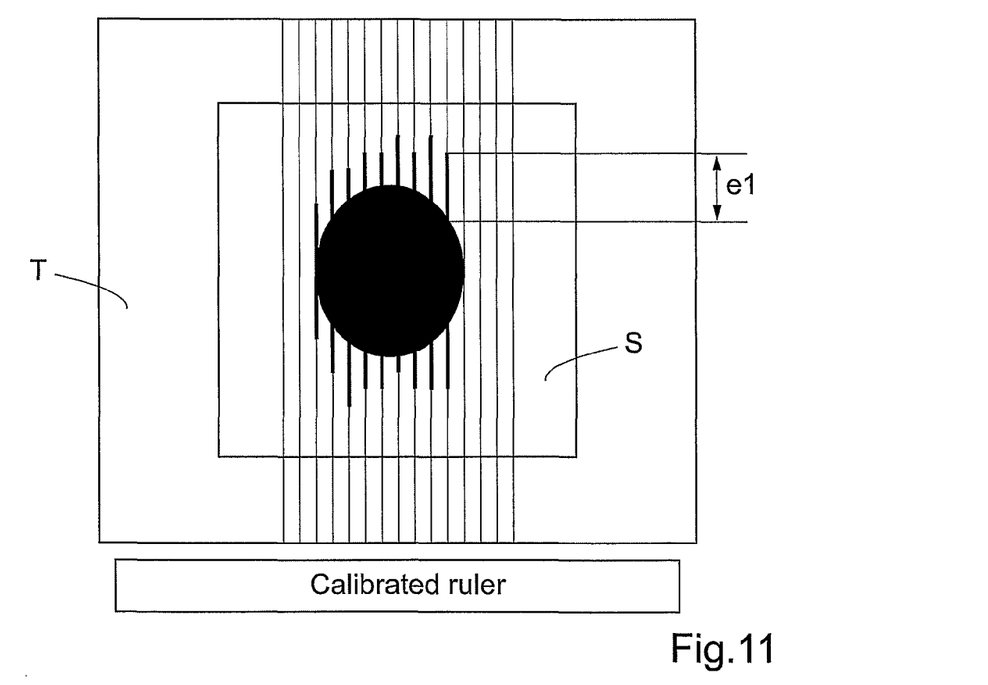

The photograph is used to measure the following distances. For all the grooves that are in contact with the hole on the sample, that is to say in all the grooves into which fluid may be expected to penetrate, the distance d from the edge next to the hole to the edge on the end of the sample is measured; see FIG. 10, which indicates this distance d1 for one of the grooves. All these distances d are then added together, and they constitute the total distance for which it is possible for the sample to leak. After this, the distance e for which the test fluid has leaked in all the grooves on the plate is measured; see FIG. 11, which shows the distance e1 for one of the grooves. The combined length of all the distances e represents the total leakage distance.

Finally, the leakage is obtained by dividing the combined leakage distance e by the total distance d for which it is possible for the sample to leak. This quotient is then converted into a percentage figure by multiplying it by 100. The evaluation of the sealing is performed as follows: Result>10% leakage, regarded as leakage. Result≦10% leakage, regarded as sealing.

Note that, between each measurement performed on the test plate, the plate must be cleaned in the following way. The plate is first rinsed with water, and it is then washed with n-heptane. It is important to ensure that no adhesive residues remain in the grooves on the plate, and a soft material of the nonwoven compress type (Mesoft®, Molnlycke Health Care) can be dipped in n-heptane and used to rub away adhesive residues in the grooves on the plate. Finally, the plate must be left to dry in the air before it can be reused.

Other solvents may be used for adhesives that are not soluble in n-heptane.

The reason why the test piece should be studied for a time after application is that any leakage will take place by means of capillary action, which means that it may be difficult to determine whether or not the test piece is leakproof immediately after application.

The above-mentioned test method with a groove depth of 75 micrometres in the grooves of the aluminium plate has demonstrated that a test piece comprising a transparent polyethylene film having a thickness of 25+/−5 micrometres with an adhesive coating of a skin friendly adhesive having a weight per unit area of ca 50 g/m$^2$ and a softness of ca 20 mm is leakproof in accordance with this test. It has also been found that a test piece with such an adhesive coating is leakproof on the normal, smooth skin of younger and middle-aged persons. It may accordingly be necessary, in areas of wrinkled skin, to use weights per unit area greater than 50 g/m$^2$ in order to ensure resistance to leakage.

The effect of the resistance to leakage on the softness and the weight per unit area of the adhesive in the adhesive coating has been investigated by the above method in respect of a silicone elastomer, Silgel 612, supplied by Wacker Chemie GmbH, Germany.

In accordance with the MHC Leakage Test with a groove depth of 75 micrometres, the leakage was measured for a number of different film dressings with different softness values and weights per unit area for the adhesive. All the dressings were manufactured by coating a polyurethane film with a thickness of 25±5 micrometres with Silgel 612 with different softness values and weights per unit area. The result is shown in FIG. 18.

The results clearly indicate the existence of a link between the softness (penetration) and the weight per unit area of the silicone elastomer. The softer the silicone elastomer, the smaller the weight per unit area required for sealing. The results point to the fact that, for a sufficient number of measurements, it is possible to produce a curve that indicates exactly the minimum weight per unit area that is required at a given softness to ensure sealing against the skin. The results make it clear that such a curve has a steep incline initially, that is to say in the case of less soft adhesives, after which it levels out. Accordingly, the relationship between the weight per unit area and the softness is such that, in order to achieve sealing at low weights per unit area, very soft adhesives are required, whereas less soft adhesives require higher weights per unit area in order to achieve sealing. It is obvious that it is difficult, and perhaps even impossible, to achieve fluid-tight film dressings at softness values below 10 mm. At softness values in the order of 20 mm, a weight per unit area of 50 g/m$^2$ may be sufficient to achieve sealing.

It should be added that all the known film dressings that were tested were found to leak.

Figure 18:
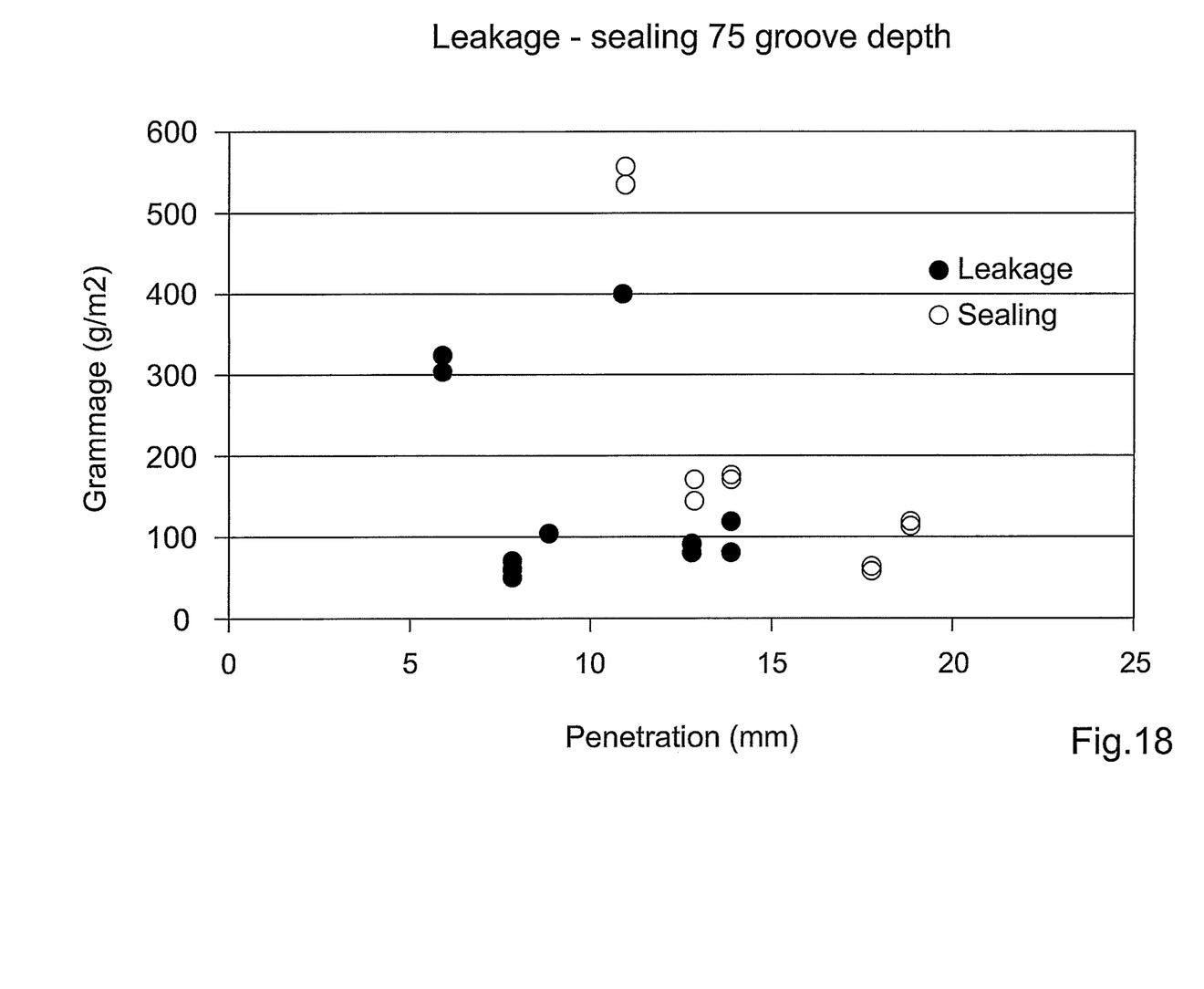
FIG. 18 shows the result of the MHC Leakage Test.

As can be appreciated from FIG. 18, certain points coincide because a number of the tested film dressings had approximately the same weights per unit area and softness values.

Apart from increasing the resistance to leakage, a higher weight per unit area for the adhesive coating is associated with a reduced risk of blisters, pimples or other damage occurring on the skin at the edges of the applied adhesive. Such damage can arise in conjunction with movements in the film dressing carrier, which lead to relative movement between the skin and the adhesive coating, or as a consequence of the dressing being subjected to external loadings, for example in the event of the film dressing carrier knocking against an object. It has been found that the risk of such damage occurring is reduced with a higher weight per unit area and a higher softness for the adhesive coating. This is presumably attributable to the fact that a proportion of the loading is absorbed by the adhesive layer through deformation and is not transmitted to the skin in this way. The film dressing in accordance with the invention is also capable of stretching together with the skin, which reduces the risk of shearing occurring between the skin and the adhesive that can give rise to mechanical damage to the skin.

In order to ensure that only a low application force is required in conjunction with the application of film dressings in accordance with the present invention, it is recommended that the softness of the soft, skin friendly adhesive that is used should be greater than 10 mm, and that it should preferably lie between 12 and 17 mm. The softer an adhesive, the more rapidly it will flow into any unevennesses in the substrate, which means that the film dressings in accordance with the present invention are leakproof immediately after their application to normal skin. At a softness value greater than 17 mm, there is a risk of the inner cohesion of the adhesive being too low, so that residues of adhesive are left behind on the skin in conjunction with the removal of an applied film dressing.

Figure 19:
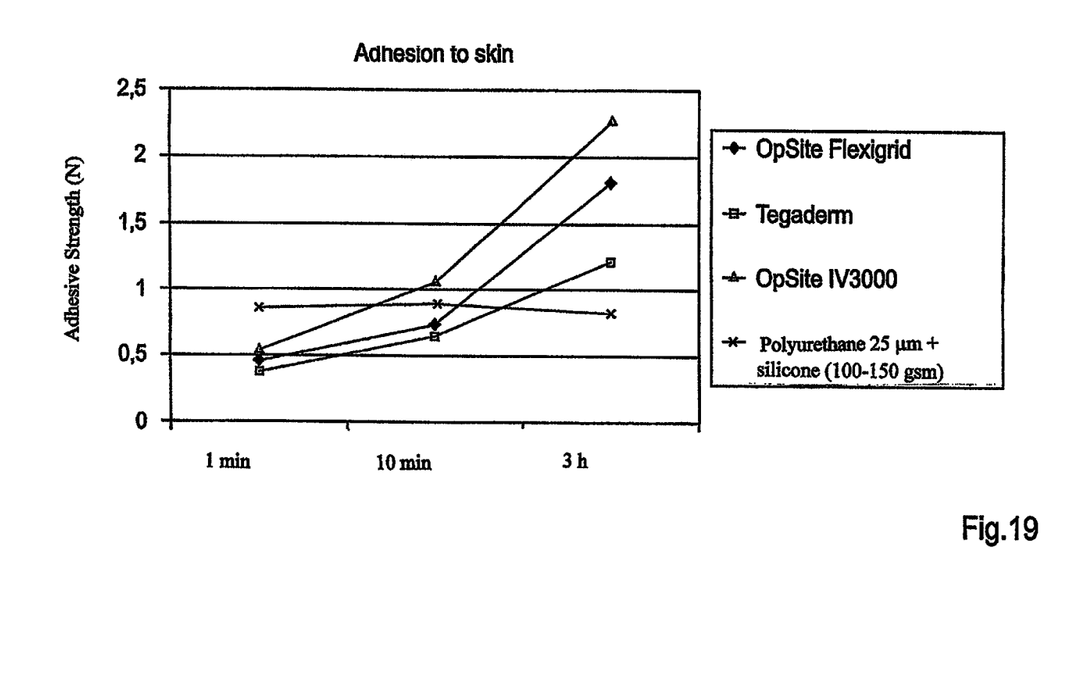
FIG. 19 shows the adhesive strength as a function of the time for a plurality of dressings.

Another important characteristic of a film dressing in accordance with the invention is that the strength of adhesive attachment of the soft, skin friendly adhesives that are used in these dressings does not change with time or changes only to a minor degree with time. This has been verified by measuring the strength of adhesive attachment to the skin for a number of known film dressings and a film dressing in accordance with the invention containing silicone elastomer as an adhesive. The known film dressings were Tegaderm® from 3M Health Care, USA; OpSite™ IV3000™ and OpSite™ Flexigrid™ from Smith & Nephew Medical Limited, England. Measurement was carried out by means of the method described above for the measurement of the strength of adhesive attachment to the skin, with the difference that the measurements were performed after 1 minute, 10 minutes and 3 hours. The results are shown in FIG. 19. As can be appreciated from this Figure, the strength of adhesive attachment increased steeply with time for the known film dressings, whereas the dressing in accordance with the invention exhibited in principle unchanged adhesion. In numerical terms, the strength of adhesive attachment from 1 minute to 3 hours increased by 295% for OpSite™ Flexigrid™, 209% for Tegaderm™ and 318% for OpSite™ IV3000™.

The strength of adhesive attachment to steel for the corresponding dressings and the Mefilm® dressing from Molnlycke Health Care AB, Sweden was also measured by means of the method described below.

Figure 15:
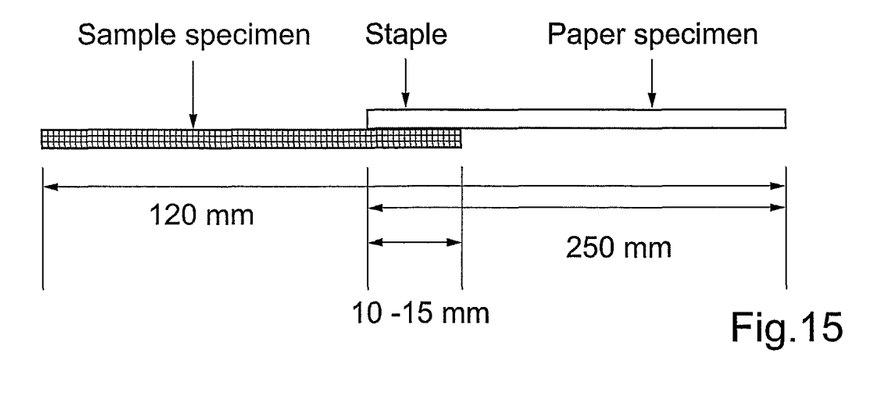
FIGS. 15-17 illustrate a method for measuring the adhesion to steel.
Figure 16:
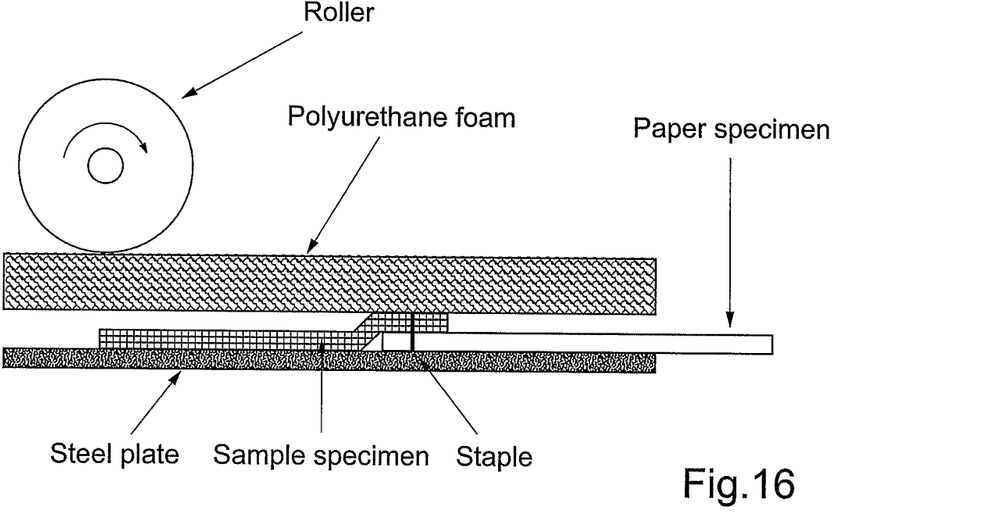

Specimens having dimensions of 25×120 mm are punched from the test material. Pieces of paper having dimensions of 25×250 mm are punched from copying paper. A steel plate (in accordance with ASTM A 666-94 A, 50×200 mm) is washed with a lint-free absorbent material saturated in n-heptane, and three washes are performed with this solvent. Finally, a final wash is performed with acetone instead of n-heptane. The steel plate is then left to dry for at least 10 minutes, but for not longer than 10 h. The piece of paper is attached to the specimen at one end against the adhesive, and the piece of paper is stapled in place using a stapler. The important consideration is for the paper to be attached to the specimen so securely that it is not able to slide off in conjunction with the application of a load. The overlap between the specimen and the piece of paper must be 10-15 mm; see FIG. 15 (view from the side). The specimen is then placed against the clean steel plate with the adhesive facing down towards the steel plate. It is important for the specimen to be laid carefully onto the steel plate in such a way that no pressure is applied to the specimen. A piece of polyurethane foam (L00562-6, 1.6 mm from Rynel, Inc., Boothbay, Me., USA) is then placed above the sample on the test plate, and the sample is attached to the plate by rolling a mangle (45 mm wide, weight=445 g, r=47 mm) back and forth once over the piece of foam 1 at a speed of 5 mm/second; see FIG. 16 (view from the side). The specimen is tested after 1 minute or 1 hour after rolling with the mangle.

Figure 17:
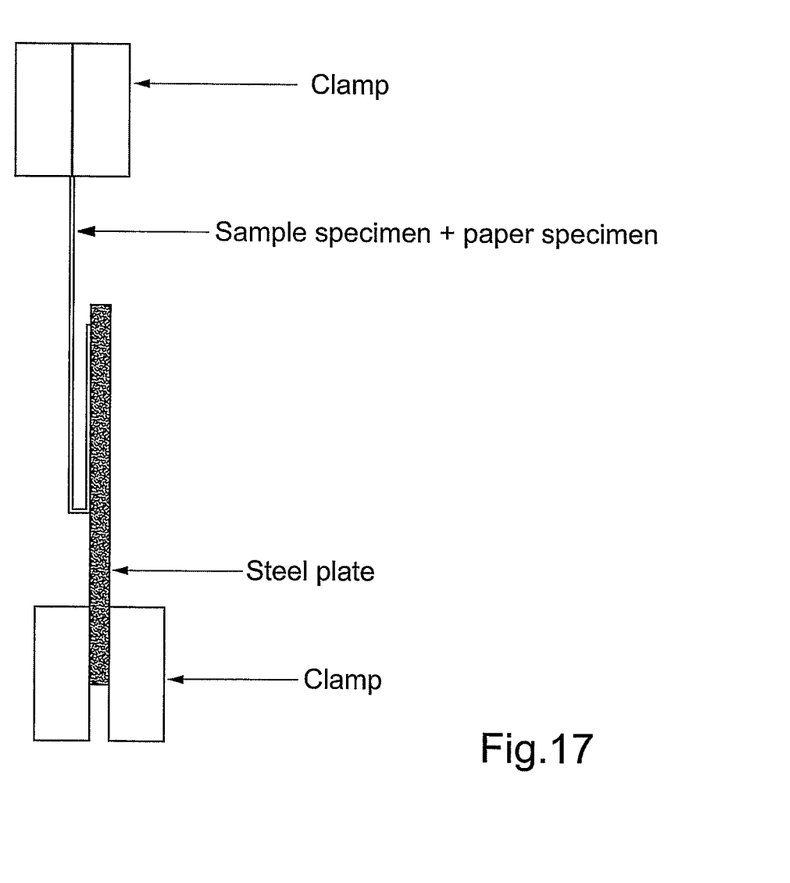

The test is performed as follows. The steel plate is clamped securely to the lower clamp of the tensile testing machine (Instron 4301, Instron 4464 or equivalent), so that the piece of paper hangs vertically downwards. The piece of paper is then folded upwards through 180 degrees and is clamped securely to the upper clamp of the tensile testing machine; see FIG. 17 (view from the side). The tensile testing machine is started, and the mean force required to pull the specimen from the steel plate is recorded. The tensile testing machine must operate at a speed of 300 mm/min.

The mean force for the different film dressings was measured after 1 minute and 1 hour. The strength of adhesive attachment increased by 22% for Tegaderm™, by 58% for Mefilm™, by 37% for OpSite™ IV3000™ and by 27% for OpSite™ Flexigrid™ after one hour, whereas no increase in the strength of adhesive attachment was measured for the film dressing in accordance with the invention.

Furthermore, no hairs are pulled out when removing film dressings provided with soft, skin friendly adhesive.

The products proposed in the present invention are normally supplied packed in sterile conditions, which means that the adhesives used must be capable of being sterilized, as must other components of such articles, of course.

The described embodiment of the invention can naturally be modified within the scope of the invention. Types of carrier layer other than the plastic layer described here can be used, for example carrier layers made of paper. It is also possible to apply an absorption body to the dressing in order to produce a so-called island dressing. It is also conceivable to apply different substances to the adhesive, for example ZnO, skin care substances or bactericidal substances, which substances are so arranged as to leak out slowly onto the skin. It is also possible to supply hydrophilic particles or similar in the adhesive. Moreover, the film may be perforated with one or more holes or may be slotted. The invention must accordingly only be restricted by the content of the following patent claims.

The invention claimed is:

1. A film dressing, comprising:
   a thin plastic film;
   an adhesive coating disposed on an entirety of one side of the thin plastic film;
   a carrier layer applied on the plastic film on a side opposite to the adhesive coating, the carrier layer removably attached to the plastic film; and
   at least one protective layer applied on the adhesive coating, the at least one protective layer removably attached to the adhesive coating,
   wherein the adhesive coating has a softness of from 10 mm to 22 mm, a weight per unit area of 50 g/m$^2$ or more, and consists of a silicone elastomer or a hot-melt adhesive, wherein a thickness of the plastic film is less than 50 micrometers, and wherein the film dressing is leak proof in accordance with the MHC Leakage Test with a groove depth of 75 micrometers.

2. The film dressing of claim 1, wherein the plastic film has a thickness of 12-25 micrometers.

3. The film dressing of claim 2, wherein the plastic film has a bending rigidity of less than 3 mm.

4. The film dressing of claim 2, wherein the plastic film has a bending rigidity of less than 1.8 mm.

5. The film dressing of claim 1, wherein a strength of adhesion to steel of an applied dressing does not vary by more than 5% during the period from 1 minute to 48 hours.

6. The film dressing of claim 1, wherein ZnO, a skin care substance, or a bactericidal substance is added to the adhesive coating.

7. The film dressing of claim 1, wherein the adhesive coating consists of a silicone elastomer.

8. The film dressing of claim 1, wherein the adhesive coating layer consists of a hot-melt adhesive.

9. A film dressing, comprising:
   a thin plastic film;
   an adhesive coating layer coated directly on one side of the thin plastic film;
   a carrier layer applied on the plastic film on a side opposite to the adhesive coating layer, the carrier layer removably attached to the plastic film; and
   at least one protective layer applied on the adhesive coating layer, the at least one protective layer removably attached to the adhesive coating layer, wherein the adhesive coating layer has a softness of from 10 mm to 22 mm, a weight per unit area of 50 g/m$^2$ or more, and consists of a silicone elastomer or a hot-melt adhesive, wherein a thickness of the plastic film is less than 50 micrometers, and wherein the film dressing is leak proof in accordance with the MHC Leakage Test with a groove depth of 75 micrometers.

10. The film dressing of claim 9, wherein the plastic film has a thickness of 12-25 micrometers.

11. The film dressing of claim 10, wherein the plastic film has a bending rigidity of less than 3 mm.

12. The film dressing of claim 10, wherein the plastic film has a bending rigidity of less than 1.8 mm.

13. The film dressing of claim 9, wherein the adhesive coating layer is free of any material other than the silicone elastomer or hot melt adhesive.

14. The film dressing of claim 9, wherein a strength of adhesion to steel of an applied dressing does not vary by more than 5% during the period from 1 minute to 48 hours.

15. The film dressing of claim 9, wherein ZnO, a skin care substance, or a bactericidal substance is added to the adhesive.

16. The film dressing of claim 9, wherein the adhesive coating layer consists of a silicone elastomer.

17. The film dressing of claim 9, wherein the adhesive coating layer consists of a hot-melt adhesive.

* * * * *

UNITED STATES PATENT AND TRADEMARK OFFICE
CERTIFICATE OF CORRECTION

PATENT NO. : 8,497,407 B2  
APPLICATION NO. : 11/794988  
DATED : July 30, 2013  
INVENTOR(S) : Fabo et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 252 days.

Signed and Sealed this

Fifteenth Day of September, 2015

Michelle K. Lee
*Director of the United States Patent and Trademark Office*